United States Patent [19]

Morimoto et al.

[11] Patent Number: 4,990,602

[45] Date of Patent: Feb. 5, 1991

[54] ERYTHROMYCIN A DERIVATIVES

[75] Inventors: Shigeo Morimoto; Takashi Adachi, both of Kitakatsushika; Tohru Matsunaga, Ageo; Masato Kashimura; Toshifumi Asaka, both of Ageo; Yoshiaki Watanabe, Kodaira; Kaoru Sota, Tokorozawa; Kazuto Sekiuchi, Ageo, all of Japan

[73] Assignee: Taisho Pharmaceutical Co., Ltd., Japan

[21] Appl. No.: 283,387

[22] Filed: Dec. 12, 1988

Related U.S. Application Data

[63] Continuation of Ser. No. 132,258, Dec. 14, 1987, abandoned.

[30] Foreign Application Priority Data

Dec. 17, 1986 [JP] Japan .................. 61-300653

[51] Int. Cl.$^5$ ........................... C07H 17/08
[52] U.S. Cl. ........................ 536/7.4; 536/7.2
[58] Field of Search ............... 536/7.4, 7.2, 7.3

[56] References Cited

U.S. PATENT DOCUMENTS 4,640,910  2/1987  Faubl et al. .................. 536/7.2
4,670,549  6/1987  Morimoto et al. ............. 536/7.4

FOREIGN PATENT DOCUMENTS 0158467 10/1985  European Pat. Off. .
0201166 11/1986  European Pat. Off. .
0222353  5/1987  European Pat. Off. .

Primary Examiner—Ronald W. Griffin
Assistant Examiner—Elli Peselev
Attorney, Agent, or Firm—Lorusso & Loud

[57] ABSTRACT

Erthromycin A derivatives represented by the general formula

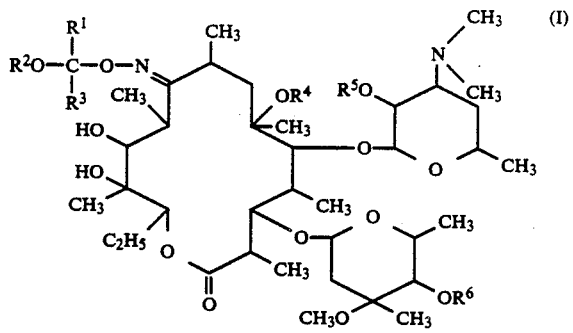

wherein $R^1$ is a group of the formula $R^7CH_2$— (wherein $R^7$ is a hydrogen group or a lower alkyl group) or a group of the formula $R^8O$— (wherein $R^8$ is a lower alkyl group), $R^2$ is $R^8$, a cycloalkyl group, a phenyl group or an aralkyl group.), or $R^2$ and $R^7$ together form an alkylene group, $R^3$ is a hydrogen atom, a lower alkyl group, a phenyl group or an aralkyl group, or $R^3$ and $R^7$ together form an alkylene group, or $R^2$ and $R^3$ together form an alkylene group, $R^4$ is a lower alkyl group, $R^5$ is a substituted silyl group, and $R^6$ is a hydrogen atom or $R^5$, are disclosed. These compounds are useful as intermediates for the synthesis of antibacterial agents.

3 Claims, No Drawings

ERYTHROMYCIN A DERIVATIVES

CROSS REFERENCE TO THE RELATED APPLICATION

This is a continuation-in-part application of U.S. Ser. No. 132,258 filed Dec. 14, 1987, now abandoned.

BACKGROUND OF THE INVENTION

1. Field of the Invention

The present invention relates to erythromycin A derivatives and a method for the preparation of the same.

2. Description of the Prior Art

6-O-Alkylerythromycins are useful as anti-bacterial agents or intermediates for synthesis of the antibacterial agents. For example, 6-O-methylerythromycin A is not only stable under acidic conditions but also has a strong antibacterial activity when compared with erythromycin A. Especially, this compound shows an excellent effect in treatment of infections by oral administration, and therefore it is a useful antibacterial agent.

There are known in the past several methods for preparing 6-O-methylerythromycin A, for example, (1) a method which comprises substituting the hydrogen atom of the hydroxy group at the 2'-position and the methyl group of the dimethylamino group at the 3'-position of the erythromycin A derivatives by benzyloxycarbonyl group, whereafter, carrying out methylation of the hydroxy group at the 6-position, elimination of the benzyloxy carbonyl group, and methylation of the methylamino group at the 3'-position (U.S. Pat. No. 4,331,803), and (2) an improved method for the selective methylation of the hydroxy group at the 6-position of erythromycin A derivatives which comprises converting erythromycin A derivatives having the protected hydroxy group at the 2'-position and/or the protected dimethylamino group at the 3'-position into the various kinds of the substituted oxime derivative, whereafter, carrying out methylation of the hydroxy group at the 6-position, elimination of the protecting groups, deoximation at the 9-position and reproduction of the dimethylamino group at the 3'-position to give 6-O-methylerythromycin A (European Pat. No. 158,467).

However, since erythromycin A has many hydroxy groups, there are obtained various kinds of erythromycin A derivatives which are methylated at hydroxy other than the 6-position as the by-products by the method of item (1). Accordingly, this method requires a complicated procedure for purification of the 6-O-methylerythromycin A derivative, and has the drawback of giving a low yield of said derivative. Although it is possible to methylate selectively the 6-hydroxy group by the method of item (2), this method requires complicated procedures such as catalytic reduction for elimination of the protecting groups after methylation.

SUMMARY OF THE INVENTION

As a result of research to solve the drawbacks of the above known methods, the present inventors have found a method for the preparation of 6-O-alkylerythromycin A derivatives by which the hydroxy group at the 6-position of erythromycin A derivatives can be methylated selectively, and introduction and elimination of the protecting groups can be easily carried out.

DETAILED DESCRIPTION OF THE INVENTION

An object of the present invention is to provide erythromycin A derivatives represented by the general formula

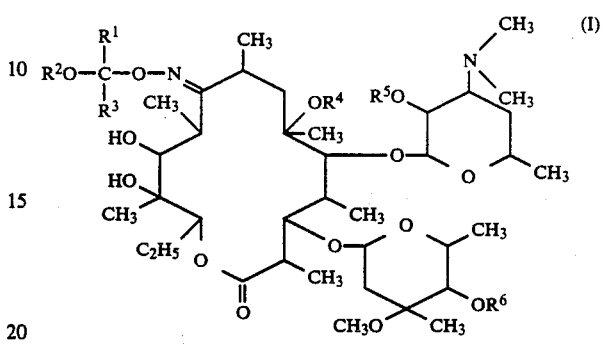

wherein $R^1$ is a group of the formula $R^7CH_2$— (wherein $R^7$ is a hydrogen atom or an alkyl group having 1 to 3 carbon atoms.) or a group of the formula $R^8O$— (wherein $R^8$ is an alkyl group having 1 to 6 carbon atoms), $R^2$ is $R^8$, a cycloalkyl group having 5 to 7 carbon atoms, a phenyl group or an aralkyl group, or $R^2$ and $R^7$ together form an alkylene group having 2 or 3 carbon atoms, $R^3$ is a hydrogen atom, an alkyl group having 1 to 4 carbon atoms, a phenyl group or an aralkyl group, or $R^3$ and $R^7$ together form an alkylene group having 3 to 5 carbon atoms which may be optionally substituted by 1 to 3 alkyl groups having each to 3 carbon atoms, or $R^2$ and $R^3$ together form an alkylene group having 3 or 4 carbon atoms, $R^4$ is an alkyl group having 1 to 3 carbon atoms, $R^5$ is a substituted silyl group of formula $-SiR^9R^{10}R^{11}$ (wherein $R^9$, $R^{10}$ and $R^{11}$ are the same or different, and each is a hydrogen atom, an alkyl group having 1 to 15 carbon atoms, a phenyl substituted alkyl group in which the alkyl moiety has 1 to carbon atoms, a phenyl group, a cycloalkyl group having to 7 carbon atoms or an alkenyl group having 2 to 5 carbon atoms, with the proviso that at least one of $R^9$, $R^{10}$ and $R^{11}$ is other than hydrogen atom), and $R^6$ is a hydrogen atom or $R^5$.

Another object of the present invention is to provide erythromycin A derivative represented by the general formula

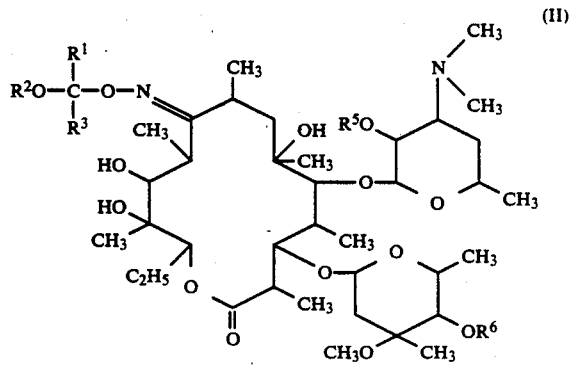

wherein $R^1$, $R^2$, $R^3$, $R^5$ and $R^6$ are as defined above.

Still another object of the present invention is to provide a method for preparing erythromycin A derivative represented by the general formula (I) which comprises reacting erythromycin A 9-oxime, in any desired sequence, with a compound of formula represented by the general formula

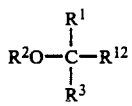

wherein $R^1$, $R^2$ and $R^3$ are as defined above, and $R^{12}$ is a group of formula $-OR^8$ (wherein $R^8$ is as defined above), or $R^1$ and $R^{12}$ together form a group of formula $R^7CH=$ (wherein $R^7$ is as defined above), and with a silylating agent having $R^5$ to give a compound formula II, and then reacting the resulting compound with an alkylating agent having $R^4$.

In the present invention, the term "alkyl group" refers to a linear or branched chain alkyl group such as, for example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group and the like. The term "aralkyl group" refers to a benzyl group, a benzyl group substituted by a methyl group, an α-methylbenzyl group, a phenethyl group and the like. Examples of the alkylene group having 2 or 3 carbon atoms are an ethylene group, a propylene group and a trimethylene group. Examples of the alkylene group having 3 to 5 carbon atoms substituted by 1 to 3 alkyl groups having each 1 to 3 carbon atoms are a 2-methyltrimethylene group, a 3-methyltrimethylene group, a 1-methyltetramethylene group, a 3-methyltetramethylene group, a 2,2,4-trimethyltetramethylene group, a 2,4,4-trimethyltetramethylene group, a 1-isopropyl-4-methyltetramethylene group and the like. The term "halogen atom" means a chlorine atom, a bromine atom, an iodine atom and the like. Examples of the substituted silyl group are a trimethylsilyl group, a triethylsilyl group, an isopropyldimethylsilyl group, a tert-butyldimethylsilyl group, a (triphenylmethyl)dimethylsilyl group, a tert-butyldiphenylsilyl group, a diphenylmethylsilyl group, diphenylvinylsilyl group, a methyldiisopropylsilyl group, a tribenzylsilyl group, a tri(p-xylyl)silyl group, a triphenylsilyl group, a diphenylsilyl group, a dimethyloctadecylsilyl group and the like.

The present invention is illustrated below in more detail. At first, erythromycin A 9-oxime is reacted with the compound of formula III to protect the hydroxy group at the 9-oxime position. This reaction may be the same as those usually employed for introduction of the protecting groups of acetal-type to a hydroxyl group. For example, erythromycin A 9-oxime is reacted with the compound of formula III in a solvent in the presence of a catalyst with stirring to give a compound of the general formula

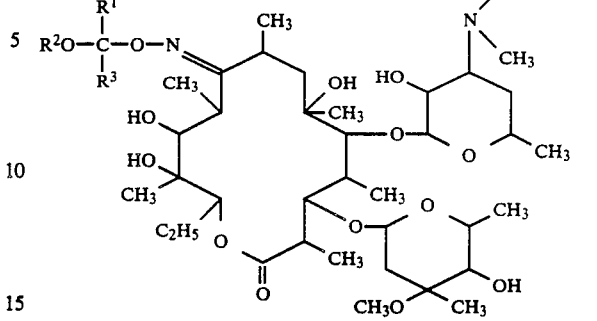

wherein $R^1$, $R^2$ and $R^3$ are as defined above. In this reaction, the amount of the compound of formula III is 2 to 20 equivalents, preferably 2 to 10 equivalents relative to erythromycin A 9-oxime.

Examples of the compounds of formula III are methyl vinyl ether, ethyl vinyl ether, n-propyl vinyl ether, isopropyl vinyl ether, n-butyl vinyl ether, isobutyl vinyl ether, 2-methoxypropene, 2-ethoxypropene, 2-n-propoxypropene, 2-isopropoxypropene, 2-n-butoxypropene, 2-isobutoxypropene, 2-sec-butoxypropene, 2-n-pentoxypropene, 2-n-hexyloxypropene, 2-benzyloxypropene, 2-methoxy-1-butene, -ethoxy-1-butene, 2-n-propoxy-1-butene, 2-isopropoxy-1-butene, 2-n-butoxy-1-butene, 2-methoxy-2-butene, 2-ethoxy-2-butene, 2-n-propoxy-2-butene, 2-isopropoxy-2-butene, 2-n-butoxy-2-butene, 2-methoxy-3-methyl-1-butene, 2-ethoxy-3-methyl-1-butene, 2-n-propoxy-3-methyl-1-butene, 2-isopropoxy-3-methyl-1-butene, 2-n-butoxy-3-methyl-1-butene, 2-methoxy-3,3-dimethyl-1-butene, 2-ethoxy-3,3-dimethyl-1-butene, 2-n-propoxy-3,3-dimethyl-1-butene, 3-methoxy-2-pentene, 3-ethoxy-2-pentene, 3-n-propoxy-2-pentene, 2-methoxy-4-methyl-2-pentene, 2-ethoxy-4-methyl-2-pentene, 2-n-propoxy-4-methyl-2-pentene, 1-methoxy-1-cyclopentene, 1-ethoxy-1-cyclopentene, 1-n-propoxy-1-cyclopentene, 1-n-butoxy-1-cyclopentene, 1-methoxy-3-methyl-1-cyclopentene, 1-methoxy-4-methyl-1-cyclopentene, 1-methoxy-1-cyclohexene, 1-ethoxy-1-cyclohexene, 1-n-propoxy-1-cyclohexene, 1-n-butoxy-1-cyclohexene, 1-methoxy-4-methyl-1-cyclohexene, 1-methoxy-6-methyl-1-cyclohexene, 1-methoxy-3,5,5-trimethyl-1-cyclohexene, 1-methoxy-3,3,5-trimethyl-1-cyclohexene, 1-methoxy-3-methyl-6-isopropyl-1-cyclohexene, 1-methoxy-1-cycloheptene, 1-ethoxy-1-cycloheptene, 1-n-propoxy-1-cycloheptene, 1-n-butoxy-1-cycloheptene, 1,1-dimethoxycyclopentane, 1,1-diethoxycyclopentane, 1,1-dimethoxycyclohexane, 1,1-diethoxycyclohexane, 1,1-dimethoxycycloheptane, 1,1-diethoxycycloheptane, 2-methylenetetrahydrafuran, 5-methyl-2,3-dihydrofuran, 2-methylenetetrahydropyran, 6-methyl-3,4-dihydro-2H-pyran, 2,2-dimethoxypropane, 2,2-diethoxypropane, 2,2-di-n-propoxypropane, 2,2-diisopropoxypropane, 2,2-di-n-butoxypropane, 2,2-diisobutoxypropane, 2,2-di-sec-butoxypropane, 2,2-di-n-pentoxypropane, 2,2-di-n-hexyloxypropane, 2,2-dimethoxybutane, 2,2-diethoxybutane, 2,2-di-n-propoxybutane, 2,2-diisopropoxybutane, 2,2-di-n-butoxybutane, 2,2-dimethoxy-3-methylbutane, 2,2-diethoxy-3-methylbutane, 2,2-di-n-propoxy-3-methylbutane, 2,2-diisopropoxy-3-methylbutane, 2,2-dimethoxypentane, 2,2-diethoxypentane, 2,2-di-n-propoxypentane, 2,2-diisopropoxypentane, 2,2- di-n-butoxypentane, 3,3-dimethoxypentane, 3,3-diethoxypentane, 3,3-di-n-propoxypentane, 3,3-diisopropoxypentane, 3,3-di-n-butoxypentane, 2,2-dimethoxy-4-methylpentane, 2,2-diethoxy-4-methylpentane, 2,2-di-n-propoxy-4-methylpentane, 2,2-diisopropoxy-4-methylpentane, 2,2-di-n-butoxy-4-methylpentane, 2,4-dimethyl-3,3-dimethoxypentane, 2,4-dimethyl-3,3-diethoxypentane, 2,4-dimethyl-3,3-di-n-propoxypentane, 2,4-dimethyl-3,3-diisopropoxypentane, 2,4-dimethyl-3,3-di-n-butoxypentane, 2,2-dimethoxyhexane, 2,2-diethoxyhexane, 2,2-di-n-propoxyhexane, 2,2-diisopropoxyhexane, 2,2-di-n-butoxyhexane, 3,3-dimethoxyhexane, 3,3-diethoxyhexane, 3,3-di-n-propoxyhexane, 3,3-diisopropoxyhexane, 3,3-di-n-butoxyhexane, trimethyl orthoformate, trimethyl orthoacetate, trimethyl orthopropionate, trimethyl orthobutyrate, trimethyl orthobenzoate, trimethyl orthophenylacetate, triethyl orthoformate, triethyl orthoacetate, triethyl orthopropionate, triethyl orthobutyrate, triethyl orthobenzoate, triethyl orthophenylacetate, tri-n-propyl orthoformate, triisopropyl orthoformate, tri-n-butyl orthoformate, tri-n-pentyl orthoformate, tri-n-hexyl orthoformate and the like.

The compounds of formula I wherein both $R^1$ and $R^3$ are methyl groups may be also prepared in the presence of 2-methoxypropene with an alcohol having $R^2$ such as, for example, ethanol, n-propanol, isopropanol, n-butanol, isobutanol, sec-butanol, n-pentanol, isopentanol, hexanol, cyclopentanol, cyclohexanol, cycloheptanol, phenol, benzyl alcohol, phenethyl alcohol, α-methylbenzyl alcohol, o-methylbenzyl alcohol, p-methylbenzyl alcohol and the like.

Examples of the solvent used for the reaction of erythromycin A 9-oxime with the compound of formula III are dichloromethane, chloroform, tetrahydrofuran, N,N-dimethylformamide, dimethyl sulfoxide, acetone, acetonitrile, nitroethane, toluene and the like. Examples of the catalyst are salts of tert-amines (e.g., pyridine, triethylamine and the like) with hydrochloric acid, sulfonic acid, p-toluenesulfonic acid and the like, preferably pyridine hydrochloride and pyridinium p-toluenesulfonate. The amount of the catalyst is 1.5 to 5 equivalents, preferably 1.5 to 2 equivalents relative to erythromycin A 9-oxime. The reaction temperature is from 0° C. to the reflux temperature of the solvent, but usually the reaction proceeds sufficiently at room temperature.

The reaction of the compound of formula IV with the silylating agent is carried out in a solvent at 0° C. to the reflux temperature of the solvent, preferably at room temperature with stirring. Examples of the silylating agent used are chlorosilanes such as trimethylchlorosilane, tert-butyldimethylchlorosilane and the like; silylamines such as 1,1,1,3,3,3-hexamethyldisilazane, trimethylsilylimidazole, N,N-dimethylaminotrimethylsilane and the like; silylamides such as bis(trimethylsilyl)acetamide, trimethylsilyldiphenylurea, bis(trimethylsilyl)urea and the like or a mixture thereof. When using one of the chlorosilanes only, it is preferable to add a base. The amount of the silylating agent used is 1 to 10 equivalents, preferably 1 to 5 equivalents relative to the compound of formula IV.

Examples of the solvent used for the reaction are acetone, tetrahydrofuran, N,N-dimethylformamide, dimethyl sulfoxide, dioxane, 1,2-dimethoxyethane, dichloromethane, chloroform and the like. Examples of the base are inorganic bases such as sodium hydroxide, potassium hydroxide, sodium carbonate, potassium carbonate, sodium bicarbonate, potassium bicarbonate and the like; and organic bases such as trimethylamine, triethylamine, tri-n-butylamine, tribenzylamine, diisopropylethylamine, N,N-dimethylaniline, pyridine, 1,8-diazabicyclo[5,4,0]unde-7-cene, imidazole and the like.

The silylamines can be preferably used together with the chlorosilanes or together with ammonium chloride or pyridine hydrochloride.

Alternatively, the compound of formula II can be obtained by acetalization after silylation of erythromycin A 9-oxime. More specifically, erythromycin A 9-oxime is reacted with the silylating agent under the same silylation conditions as described above, and then the resulting compound is reacted with the compound of formula III under the same acetalization conditions as described above to give the compound of formula II.

The alkylation of the 6-hydroxy group can be carried out by the reaction of the compound of formula II with the alkylating agent in a solvent in the presence of a base at −15° C. to room temperature, preferably at 0° C. to room temperature with stirring. Examples of the alkylating agent are methyl bromide, ethyl bromide, n-propyl bromide, methyl iodide, ethyl iodide, n-propyl iodide, dimethyl sulfate, diethyl sulfate, di-n-propyl sulfate, methyl p-toluenesulfonate, ethyl p-toluenesulfonate, n-propyl p-toluenesulfonate, methyl methanesulfonate, ethyl methanesulfonate, n-propyl methanesulfonate and the like. It is sufficient to use 1 to 3 molar equivalents of the methylating agent relative to the compound of formula II. Examples of the solvents used are polar aprotic solvents such as N,N-dimethylformamide, dimethyl sulfoxide, N-methyl-2-pyrrolidone, hexamethylphosphoric triamide, a mixture thereof or a mixture of one of these solvents and a solvent such as tetrahydrofuran, 1,2-dimethoxyethane, acetonitrile, ethyl acetate and the like. Examples of the base are sodium hydroxide, potassium hydroxide, sodium hydride, potassium tert-butoxide, potassium hydride and the like. The amount of the base used is usually 1 to 2 equivalents relative to the compound of formula II.

Although erythromycin A 9-oxime derivatives of the present invention exist as two isomers (syn- and anti-forms), for the purpose of the present invention, these compounds may exist as either of the isomers or as a mixture thereof.

According to the method of the present invention, since the 2'-hydroxy group is silylated, alkylation of the 6-hydroxy group prevents the 3'-dimethylamino group from quaternarizing. Therefore, it is not necessary to protect the 3'-dimethylamino group.

The methylation of the hydroxy group at the 6-position of the present invention has good selectively, as good as the prior art method.

Furthermore, the protecting groups of the hydroxy groups at the oxime, 2'- and 4"-positions of the compound of formula II of the present invention can be easily eliminated under acidic conditions.

Furthermore, since the reproduction of ketone by deoximation can be carried out under acidic conditions in good yield, this process can be done conveniently at the same time as the above elimination of the protecting groups.

Therefore, according to the method of the present invention, the reaction procedure is extremely simplified and 6-O-alkylerythromycin A can be obtained in high yield and economically. More specifically, the compound of formula I can be converted to 6-O-alkylerythromycin A, for example, by the following method.

The protecting groups of the hydroxy groups at the oxime, 2'- and 4"-positions of the compound of formula I can be easily eliminated in a suitable organic solvent in the presence of water and an acid at room temperature to the reflux temperature of the solvent with stirring. Examples of the acid are formic acid, acetic acid, n-propionic acid, oxalic acid, malonic acid, succinic acid and the like. Examples of the organic solvent are hydrophilic solvents such as methanol, ethanol, isopropanol, dioxane, tetrahydrofuran, N,N-dimethylformamide and the like.

6-O-Alkylerythromycin A 9-oxime thus obtained can be easily converted into 6-O-alkylerythromycin A by reaction with a deoximating agent. Examples of the deoximating agent are inorganic sulfur oxide compounds such as sodium hydrogen sulfite, sodium pyrosulfate, sodium thiosulfate, sodium sulfite, sodium hydrosulfite, sodium metabisulfite, sodium dithionate, potassium hydrogen sulfite, potassium thiosulfate, potassium metabisulfite and the like. Examples of the solvent used in the reaction are the same hydrophilic solvents as those used for the elimination of the silyl groups described above. Coexistence of an acid makes the speed of the reaction much faster. In the present invention, the reaction of the compound of formula I with the deoximating agent in the presence of the acid brings about conveniently the deoximation together with the elimination of the protecting groups described above. For example, to the compound of formula I is added formic acid or sodium hydrogen sulfite in aqueous ethanol, and the mixture is stirred at 50° C. to the reflux temperature to give 6-O-alkylerythromycin A. The amount of formic acid is 1.5 to 10 equivalents, preferably 2 to 5 equivalents relative to the compound of formula I, and the amount of sodium hydrogen sulfite is 1 to 10 equivalents, preferably 4 to 7 equivalents relative to the compound of formula I. The intermediates in any steps can be isolated from the reaction solution, for example, by extraction, and further can be purified by recrystallization, column chromatography and the like. However, it is not essential to follow these isolation and purification procedures.

Since the progress of the reaction can be monitored by using thin layer chromatography or high speed liquid chromatography, the reaction may be stopped after the disappearance of the starting material.

Next, the present invention will be illustrated by the following Examples.

EXAMPLE 1

(1) To a solution of 5 g of erythromycin A 9-oxime in 100 ml of dichloromethane were added 6.4 ml of 2-methoxypropene and 1.15 g of pyridine hydrochloride, and the mixture was stirred at room temperature for 15 minutes. After completion of the reaction, 100 ml of a saturated aqueous sodium bicarbonate solution was added, the mixture was thoroughly stirred, and the organic layer was separated from the aqueous layer. The aqueous layer was extracted once more with 50 ml of dichloromethane. The combined organic layer was washed with saturated aqueous sodium chloride solution and dried over anhydrous magnesium sulfate, and then the solvent was evaporated under reduced pressure. To the residue was added 50 ml of benzene, and the solvent was evaporated under reduced pressure. The procedure was repeated three times to give 5.15 g of erythromycin A 9-[O-(1-methoxy-1-methylethyl)oxime] as a foam.

m.p. 113°–116° C. (recrystallized from diethyl ether-petroleum ether)

$^1$H-NMR (CDCl$_3$);
δ (ppm) = 2.30 [3'-N(CH$_3$)$_2$], 3.23
[-OC(CH$_3$)$_2$OC$\underline{H}_3$], 3.33 (3"-OCH$_3$)
$^{13}$C-NMR (CDCl$_3$);
δ (ppm) = 23.9 and 24.0 [-O-C($\underline{C}$H$_3$)$_2$OCH$_3$],
40.3 [3'-N(CH$_3$)$_2$], 49.5
[-O-C(CH$_3$)$_2$O$\underline{C}$H$_3$ and 3"-OCH$_3$],
103.7 [-O-$\underline{C}$(CH$_3$)$_2$OCH$_3$]

(2) To a solution of 4.1 g of the compound, obtained above, in 40 ml of dichloromethane was added a solution of 1.8 ml of trimethylsilylimidazole and 1.0 ml of trimethylchlorosilane in 5 ml of dichloromethane, and the mixture was stirred at room temperature for 10 minutes. To the reaction solution was added 60 ml of n-hexane, and the precipitate was removed by filtration. The filtrate was concentrated under reduced pressure. To the residue was added 50 ml of a saturated aqueous sodium bicarbonate solution, and the mixture was extracted with dichloromethane (50 ml×2). The organic layer was washed with saturated aqueous sodium chloride solution and dried over magnesium sulfate. The solvent was evaporated under reduced pressure to give 4.5 g of 2',4"-O-bis(trimethylsilyl)-erythromycin A 9-[O-(1-methoxy-1-methylethyl)oxime] as a foam.

m.p. 124°–126.5° C. (recrystallized from acetone)

$^1$H-NMR (CDCl$_3$); δ (ppm)=0.10 (2'—O—TMS), 0.14 (4"—O—TMS), 2.23 [3'-N(CH$_3$)$_2$], 3.22 [—O—C(CH$_3$)$_2$OC$\underline{H}_3$], 3.31 (3"-OCH$_3$)

$^{13}$C-NMR (CDCl$_3$); δ (ppm)=0.9 (4"—O—TMS), 1.0 (2'—O—TMS), 23.9 and 24.0 [—O—C($\underline{C}$H$_3$)$_2$OCH$_3$], 41.0 [3'-N(CH$_3$)$_2$], 49.3 [—O—C(CH$_3$)$_2$O$\underline{C}$H$_3$], 49.6 (3"-OCH$_3$), 103.5 [-O$\underline{C}$(CH$_3$)$_2$OCH$_3$]

TMS as used above and hereinafter is a trimethylsilyl group.

(3) To a solution of 2 g of the compound, obtained above, in 100 ml of a mixture of dimethyl sulfoxide and tetrahydrofuran (1:1) were added 0.208 ml of methyl iodide and 178 mg of 85% potassium hydroxide powder, and the mixture was stirred at room temperature for 100 minutes. To the reaction solution was added 1 ml of 50% aqueous dimethylamine solution, and the mixture was stirred for 1 hour. To the reaction solution was added 100 ml of water, and the mixture was extracted with ethyl acetate (100 ml and 50 ml). The organic layer was washed with a saturated aqueous sodium chloride solution and then dried over anhydrous magnesium sulfate. The solvent was evaporated under reduced pressure to give 2 g of 2',4"-O-bis(trimethylsilyl)-6-O-methylerythromycin A 9-[O-(1-methoxy-1-methylethyl)oxime] as a foam.

m.p. 134.5°–137° C. (recrystallized from chloroform acetone)

$^1$H-NMR (CDCl$_3$); δ (ppm)=0.09 (2'—O—TMS), 0.15 (4"—O—TMS), 2.23 [3'—N(CH$_3$)$_2$], 3.09 (6—OCH$_3$), 3.24 [—O—C(CH$_3$)$_2$OCH$_3$], 3.33 (3"—OCH$_3$)

$^{13}$C-NMR (CDCl$_3$); δ (ppm)=0.9 (4"—O—TMS), 1.0 (2'—O—TMS), 23.5 and 24.4 [—O—C($\underline{C}$H$_3$)$_2$OCH$_3$], 41.0 [3'-N(CH$_3$)$_2$], 49.0 [—O—C(CH$_3$)$_2$OCH$_3$], 49.7 (3"-OCH$_3$), 51.0 (6-OCH$_3$), 102.9 [—O—C(CH$_3$)$_2$OCH$_3$]

EXAMPLE 2

(1) To a solution of 14.98 g of erythromycin A 9-oxime in 300 ml of dichloromethane were added 15.36 ml of 2-methoxypropene and 3.47 g of pyridine hydrochloride, and the mixture was stirred at room temperature for 20 minutes. Subsequently, a solution of 5.08 ml of trimethylchlorosilane and 5.6 g of trimethylsilylimidazole in 10 ml of dichloromethane was added, and the mixture was stirred at room temperature for 30 minutes. After addition of water, the mixture was made basic with 2N aqueous sodium hydroxide solution and extracted with chloroform. The extract was washed with, in turn, water and a saturated aqueous sodium chloride solution and dried over anhydrous magnesium sulfate. The solvent was evaporated under reduced pressure to give 18.78 g of a foam, which was identical to the compound obtained in Example 1 (2).

(2) To a solution of 3.86 g of the compound, obtained above, in a mixture of 28 ml of dimethyl sulfoxide and 56 ml of tetrahydrofuran, were added 0.37 ml of methyl iodide and 342 mg of 85% potassium hydroxide powder, and the mixture was stirred at room temperature for 2 hours. To the reaction solution was added 2 ml of 50% aqueous dimethylamine solution, and the mixture was stirred for 30 minutes and extracted with n-hexane (150 ml and 100 ml). The organic layer was washed with, in turn, water and a saturated aqueous sodium chloride solution and dried over anhydrous magnesium sulfate. The solvent was evaporated under reduced pressure, and the residue was recrystallized from chloroform - acetone to give 3.0 g of 2',4''-O-bis(trimethylsilyl)-6-O-methylerythromycin A 9-[O-(1-methoxy-1-methylethyl)oxime], which was identical to the compound obtained in Example 1(3).

EXAMPLE 3

(1) To a solution of 7.75 g of the compound, obtained in Example 1(1), in 70 ml of N,N-dimethylformamide was added 2.17 ml of triethylamine. Then, 1.89 ml of trimethylchlorosilane was added dropwise, and the mixture was stirred at room temperature for 10 minutes. The reaction solution was poured into water and extracted with diethyl ether (150 ml x 2). The organic layer was washed with a saturated aqueous sodium chloride solution and dried over anhydrous magnesium sulfate. The solvent was evaporated under reduced pressure, and the residue was recrystallized twice from n-hexane to give 2.3 g of 2'-O-trimethylsilylerythromycin A 9-[O-(1-methoxy-1-methylethyl)oxime].

m.p. 113.5°–115° C.

$^1$H-NMR (CDCl$_3$) δ (ppm)=0.13 (2'—O—TMS), 2.24 [3'-N(CH$_3$)$_2$], 3.23 [—O—C(CH$_3$)$_2$OCH$_3$], 3.33 (3''-OCH$_3$)

(2) To a solution of 1.79 g of the compound, obtained above, in 36 ml of a mixture of dimethyl sulfoxide and tetrahydrofuran (1:1), were added under ice-cooling with stirring 0.19 ml of methyl iodide and then 171 mg of 85% potassium hydroxide powder, and the mixture was stirred at room temperature for 1.5 hours. To the reaction solution was added 1 ml of 50% aqueous dimethylamine solution, and stirring was continued for 30 minutes. The reaction solution was poured into water and extracted with n-hexane (70 ml×2), and the organic layer was washed with, in turn, water and a saturated aqueous sodium chloride solution and dried over anhydrous magnesium sulfate. The solvent was evaporated under reduced pressure, and the residue was recrystallized from acetone to give 1.32 g of 6-O-methyl-2'-O-trimethylsilylerythromycin A 9-[O-(1-methoxy-1-methylethyl)oxime].

m.p. 123°–125.5° C.

$^1$H-NMR (CDCl$_3$); δ (ppm)=0.10 (2'—O—TMS), 2.23 [3'-N(CH$_3$)$_2$], 3.09 (6—OCH$_3$), 3.23 [—O—C(CH$_3$)$_2$OCH$_3$], 3.34 (3''—OCH$_3$)

EXAMPLE 4

(1) To a solution of 2 g of erythromycin A 9-oxime in 40 ml of dichloromethane were added 2.3 g of 2-ethoxypropene and 0.46 g of pyridine hydrochloride, and the mixture was stirred at room temperature for 15 minutes. Then, following a procedure similar to that of Example 1 (1), there was obtained 2.03 g of erythromycin A 9-[O-(1-ethoxy-1-methylethyl)oxime] as a foam.

m.p. 106.5°–107.5° C. (recrystallized from dichloromethane - diisopropyl ether)

$^1$H-NMR (CDCl$_3$); δ (ppm)=2.29 [3+—N(CH$_3$)$_2$], 3.33 (3''—OCH$_3$), 3.48 (—OCH$_2$CH$_3$)

$^{13}$C-NMR (CDCl$_3$); δ (ppm)=15.4 (—OCH$_2$CH$_3$), 24.2 and 24.5 [—O—C(CH$_3$)$_2$O—], 40.3 [3'—N(CH$_3$)$_2$], 49.5 (3''-OCH$_3$), 57.5 (—OCH$_3$), 103.6 [—O—C(CH$_3$)$_2$O—]

Mass (FAB): m/z=835 (MH+)

(2) To a solution of 4.18 g of the compound, obtained above, in 30 ml of dichloromethane, was added a solution of 1.4 g of trimethylsilylimidazole and 1.25 ml of trimethylchlorosilane in 5 ml of dichloromethane, and the mixture was stirred at room temperature for 20 minutes. Then, following a procedure similar to that of Example 1(2), the resulting product was recrystallized from chloroform-acetone to give 3.9 g of 2',4''-O-bis(-trimethyl)silyl)-erythromycin A 9-[O-(1-ethoxy-1-methylethyl)oxime].

m.p. 120°–122° C.

$^1$H-NMR (CDCl$_3$); δ (ppm)=0.10 (2'—O—TMS), 0.14 (4''—O—TMS), 2.23 [3'—N(CH$_3$)$_2$], 3.31 (3''—OCH$_3$)

$^{13}$C-NMR (CDCl$_3$); δ (ppm)=0.6 (4''—O—TMS), 0.7 (2'—O—TMS), 24.0 and 26.3 [—O—C(CH$_3$)$_2$O—], 40.7 [3'—N(CH$_3$)$_2$]49.3 (3''—OCH$_3$), 57.0 (—O—CH$_2$CH$_3$), 103.1 [—O—C(CH$_3$)$_2$O—]

Mass (EI): m/z=978 (M+)

(3) To a solution of 1.96 g of the compound, obtained above, in 100 ml of a mixture of dimethyl sulfoxide and tetrahydrofuran (1:1), were added 0.19 ml of methyl iodide and 171 mg of 85% potassium hydroxide powder, and the mixture was stirred at room temperature for 2 hours. Then, following procedure similar to that of Example 1(3), the resulting product was recrystallized from acetone to give 1.63 g of 2',4''-O-bis(trimethylsilyl)6-O-methylerythromycin A 9-[O-(1-ethoxy-1-methyloxime].

m.p. 127.5°–128° C.

$^1$H-NMR (CDCl$_3$); δ (ppm)=0.08 (2'—O—TMS), 0.14 (4''-O-TMS), 2.22 [340 -N(CH$_3$)$_2$], 3.08 (6-OCH$_3$), 3.32 (3''-OCH$_3$)

$^{13}$C-NMR (CDCl$_3$); δ (ppm)=0.6 (4''—O—TMS), 0.8 (2'—O—TMS), 23.8 and 24.6 [—O—C(CH$_3$)$_2$O-], 40.7 [3'-N(CH$_3$)$_2$], 49.4 (3''-OCH$_3$), 50.6 (6-OCH$_3$), 56.3 (—O—CH$_2$CH$_3$), 102.4 [—O—C(CH$_3$)$_2$O-]

Mass (EI); m/z=992 (M+)

EXAMPLE 5

(1) To a solution of 2 g of erythromycin A 9-oxime in 40 ml of dichloromethane were added 2.67 g of 2-isopropoxypropene and 0.46 g of pyridine hydrochloride, and the mixture was stirred at room temperature for 15 minutes. Then, following a procedure similar to that of Example 1(1), there was obtained 2.05 g of erythromycin A 1-{O-[1-(1-methylethoxy)-1-methylethyl]oxime}.

m.p. 105°–108° C. (recrystallized from dichloromethane - diisopropyl ether)

$^1$H-NMR (CDCl$_3$): δ (ppm)=2.29 [3'—N(CH$_3$)$_2$], 3.33 (3"—OCH$_3$), 4.00 [—O—CH(CH$_3$)$_2$]

$^{13}$C-NMR (CDCl$_3$); δ (ppm)=24.1, 24.3, 24.5 and 25.6 [—O—C(CH$_3$)$_2$O—CH(CH$_3$)$_2$), 40.3 [3'—N(CH$_3$)$_2$], 49.5 (3"—OCH$_3$), 64.6 [—OCH(CH$_3$)$_2$], 103.9 [—O—C(CH$_3$)$_2$O—]

Mass (FAB); m/z=849 (MH+)

(2) To a solution of 3 g of the compound, obtained above, in 30 ml of dichloromethane was added a solution of 1.04 ml of trimethylsilylimidazole and 0.90 ml of trimethylchlorosilane in 5 ml of dichloromethane, and the mixture was stirred at room temperature for 10 minutes. To the reaction solution were added 2N aqueous sodium hydroxide solution and water, and the organic layer was collected. The aqueous layer was extracted with dichloromethane. The combined organic layer was washed with, in turn, water and saturated aqueous sodium chloride solution and dried over anhydrous magnesium sulfate. The solvent was evaporated under reduced pressure, and the residue was recrystallized from aqueous acetone to give 2.46 g of 2',4"—O—bis(trimethylsilyl)-erythromycin A 9-{O-[1-(1-methylethoxy)-1-methylethyl]oxime}.

m.p. 93°–96° C. (recrystallized from aqueous acetone)

$^1$H-NMR (CDCl$_3$); δ (ppm)=0.10 (2'—O—TMS), 0.15 (4"—O—TMS), 2.23 [3'—N(CH$_3$)$_2$], 3.30 (3"—OCH$_3$) 4.00 [—OCH(CH$_3$)$_2$]

$^{13}$C-NMR (CDCl$_3$); δ (ppm)=0.7 (4"—O—TMS), 0.8 (2'—O—TMS), 23.9, 24.0, 24.4 and 25.3 [—O—C(CH$_3$)$_2$O—CH(CH$_3$)$_2$], 40.8 [3'—N(CH$_3$)$_2$], 49.5 (3"—OCH$_3$), 64.2 [—O—CH(CH$_3$)$_2$]103.5 [—O—C(CH$_3$)$_2$O—]

Mass (EI); m/z=992 (M+)

To a solution of 1 g of the compound, obtained above, in 10 ml of a mixture of dimethyl sulfoxide and tetrahydrofuran (1:1) were added under ice-cooling 0.08 ml of methyl iodide and 73 mg of 85% potassium hydroxide powder, and the mixture was stirred for 90 minutes. Then, following the procedure similar to that of Example 1(3), there was obtained 0.95 g of 2',4"-O-bis(trimethylsilyl)-6-O-methylerythromycin A 9-{O-[1-(1-methylethoxy)-1-methylethyl]oxime}.

m.p. 115.5°–118.5° C. (recrystallized from aqueous acetone)

$^1$H-NMR (CDCl$_3$); δ (ppm)=0.09 (2'—O—TMS), 0.15 (4"—O—TMS), 2.23 [3'—N(CH$_3$)$_2$], 3.08 (6—OCH$_3$), 3.32 (3"—OCH ), 4.08 [—OCH(CH$_3$)$_2$]

$^{13}$C-NMR (CDCl$_3$); δ (ppm)=0.8 (4"—O—TMS), 0.9 (2'—O—TMS), 24.0, 24.3, 24.7 and 25.6 [—O—C(CH$_3$)$_2$O—CH(CH$_3$)$_2$], 40.9 [3'—N(CH$_3$)$_2$], 49.6 (3"—OCH$_3$), 50.8 (6—OCH$_3$), 63.5 (—O—CH(CH$_3$)$_2$], 102.9 [—O—C(CH$_3$)$_2$O—]

Mass (EI); m/z=1006 (M+)

EXAMPLE 6

To a solution of 1 g of 2',4"-O-bis(trimethylsilyl)-erythromycin A 9-[O-(1-methoxy-1-methylethyl)oxime], obtained in Example 1(2), in 20 ml of a mixture of dimethyl sulfoxide and tetrahydrofuran (1:1), were added 0.09 ml of methyl iodide and 45 mg of 60% oily sodium hydride, and the mixture was stirred at room temperature for 2 hours. After the reaction, 0.5 ml of 50% aqueous dimethylamine solution was added, and stirring was continued for 30 minutes. 50 ml of water was added, the mixture was extracted with ethyl acetate (50 ml and 25 ml), and the organic layer was washed with a saturated aqueous sodium chloride solution and dried over anhydrous magnesium sulfate. The solvent was evaporated under reduced pressure to give 0.9 g of 2',4"-O-bis(trimethylsilyl)-6-O-methylerythromycin A 9-[O-(1-methoxy-1-methylethyl)oxime], which was identical to the compound obtained in Example 1(3).

EXAMPLE 7

In 10 ml of N,N-dimethylformamide were dissolved 2.46 g of erythromycin A 9-[O-(1-methoxy-1-methylethyl)oxime] obtained in Example 1(1) and 3.0 ml of 1,1,1,3,3,3-hexamethyldisilazane, and the solution was stirred at 60°–70° C. for 8 hours. After stirring, the mixture was allowed to stand at room temperature for 2 days, and 200 ml of ethyl acetate was added to the reaction solution, and the organic layer was washed 3 times with 100 ml of a saturated aqueous sodium chloride solution and dried over anhydrous magnesium sulfate. The solvent was evaporated under reduced pressure to give 2.6 g of 2',4"-O-bis(trimethylsilyl)-erythromycin A 9-[O-(1-methoxy-1-methylethyl)oxime] as a foam, which was identical to the compound obtained in Example 1(2).

EXAMPLE 8

To a solution of 7.49 g of erythromycin A 9-oxime in 100 ml of dichloromethane was added 9.0 ml of 2-methoxypropene. 1.74 g of pyridine hydrochloride was added at room temperature with stirring, and the mixture was stirred at room temperature for 1 hour. To the mixture was added 1.25 ml of 1,1,1,3,3,3-hexamethyldisilazane, and stirring was continued for a further 3 hours. 100 ml of dichloromethane and 100 ml of a saturated aqueous sodium carbonate solution were added, and the mixture was stirred thoroughly. The dichloromethane layer was collected, washed twice with a saturated aqueous sodium chloride solution and dried over anhydrous magnesium sulfate. The solvent was evaporated under reduced pressure, and the resulting foam was recrystallized from acetone to give 8.74 g of 2',4"-O-bis-)trimethylsilyl)-erythromycin A 9-[O-(1-methoxy-1methylethyl)oxime], which was identical to the compound obtained in Example 1(2).

EXAMPLE 9

To a solution of 1 g of erythromycin A 9-oxime in 7 ml of dichloromethane were added under ice-cooling 0.23 g of pyridine hydrochloride and then a solution of 1.3 g of 2,2-dimethoxypropane in 3 ml of dichloromethane, and the mixture was stirred at room temperature for 24 hours. After the reaction, the mixture was added to 2N aqueous sodium hydroxide solution and extracted with dichloromethane. The organic layer was washed with, in turn, water and a saturated aqueous sodium chloride solution, and dried over magnesium sulfate. The solvent was evaporated under reduced pressure to give 0.65 g of erythromycin A 9-[O-(1-methoxy-1-methylethyl)oxime] as a foam, which was identical to the compound obtained in Example 1(1).

EXAMPLE 10

(1) To a solution of 10 g of erythromycin A 9-oxime in 50 ml of N,N-dimethylformamide were added 2.31 g of pyridine hydrochloride and then 5.6 ml of 1,1,1,3,3,3- hexamethyldisilazane under ice-cooling, and the mixture was stirred at room temperature for 5 hours. After the reaction, 50 ml of 2N aqueous sodium hydroxide solution and 50 ml of water were added, and the mixture was extracted with ethyl acetate (100 ml and 50 ml).

The organic layer was washed with, in turn, water (50 ml×2) and a saturated aqueous sodium chloride solution (50 ml) and dried over anhydrous magnesium sulfate. The solvent was evaporated under reduced pressure to give 11.9 g of 2',4"-O-bis(trimethylsilyl)erythromycin A 9-oxime, which was then purified by recrystallization from aqueous acetone.

$^1$H-NMR (CDCl$_3$); δ (ppm)=0.11 (2'—O—TMS), 0.15 (4"—O—TMS), 2.21 [3'—N(CH$_3$)$_2$], 3.30 (3"—OCH$_3$), 8.05 (=N—OH)

$^{13}$C-NMR (CDCl$_3$); δ (ppm)=0.9 (4"—O—TMS), 1.0 (2'—OTMS), 41.0 [3'—N(CH$_3$)$_2$], 49.8 (3"—OCH$_3$)

Mass (EI); m/z=892 (M+)

(2) To a solution of 1 g of the compound, obtained above, in 7 ml of dichloromethane were added under ice-cooling 194 mg of pyridine hydrochloride and then 1.17 g of 2,2-dimethoxypropane, and the mixture was stirred at room temperature for 5 hours. The reaction solution was poured into dilute aqueous sodium bicarbonate solution and extracted with dichloromethane. The organic layer was washed with a saturated aqueous sodium chloride solution and dried over anhydrous magnesium sulfate. The solvent was evaporated under reduced pressure to give 0.70 g of 2',4"-O-bis(trimethylsilyl)-erythromycin A 9-[O-(1-methoxy-1-methylethyl)oxime], which was identical to the compound obtained in Example 1(2).

EXAMPLE 11

To a solution of 330 mg of erythromycin A 9-oxime in 2.3 ml of dichloromethane were added under ice-cooling 80 mg of pyridine hydrochloride and then a solution of 0.7 g of 2,2-diisopropoxypropane in 1 ml of dichloromethane, and the mixture was stirred at room temperature for 30 minutes. Then, following a procedure similar to that of Example 9, there was obtained 370 mg of erythromycin A 9-{O-[1-(1-methylethoxy)-1-methylethyl]oxime}, which was identical to the compound obtained in Example 5(1).

Example 12

To a solution of 1 g of 2',4"-O-bis(trimethylsilyl)-erythromycin A 9-oxime, obtained in Example 10(1), in 5 ml of dichloromethane were added under ice-cooling 194 mg of pyridine hydrochloride and then a solution of 449 mg of 2,2-diisopropoxypropane in 2 ml of dichloromethane, and the mixture was stirred at room temperature for 1.5 hours. Then, following the procedure similar to that of Example 10(2), there was obtained 1.1 g of 2',4"-O-bis(trimethylsilyl)-erythromycin A 9-{O-[1-(1-methylethoxy-1-methylethyl]oxime}, which was identical to the compound obtained in Example 5(2).

EXAMPLE 13

(1) To a solution of 10 g of erythromycin A 9-oxime in 40 ml of dichloromethane were added under ice-cooling 2.3 g of pyridine hydrochloride and then a solution of 6.1 g of 2-n-butoxypropene in 30 ml of dichloromethane, and the mixture was stirred at room temperature for 1 hour. Then, following the procedure similar to that of Example 1(1), there was obtained 2.75 g of erythromycin A 9-[O-(1-n-butoxy-1-methylethyl)oxime].

m.p. 93°-95° C. (recrystallized from diethyl ether-petroleum ether)

$^1$H-NMR (CDCl$_3$); δ (ppm)=0.91 [—O(CH$_2$)$_3$CH$_3$], 2.28 [3'-N(CH$_3$)$_2$], 3.32 (3"—OCH$_3$), 3.40 (—OCH$_2$CH$_2$CH$_2$CH$_3$)

Mass (FAB); m/z=865 (MH+)

(2) To a solution of 2 g of the compound, obtained above, in 20 ml of dichloromethane was added a solution of 0.68 ml of trimethylsilylimidazole and 0.59 ml of trimethylchlorosilane in 5 ml of dichloromethane, and the mixture was stirred at room temperature for 10 minutes. Then, following the procedure similar to that of Example (2), there was obtained the residue, which was then purified by Florisil column chromatography (eluent, acetone:n-hexane:triethylamine=1:5:0.01) to give 2.32 g of 2',4"-O-bis(trimethylsilyl)-erythromycin A 9-[O-(1-n-butoxy-1-methylethyl)oxime].

$^1$H-NMR (CDCl$_3$); δ (ppm)=0.09 (2'—O—TMS), 0.14 (4"—O—TMS), 0.90 [—O(CH$_2$)$_3$CH$_3$], 2.22 [3'—N(CH$_3$)$_2$], 3.30 (3"—OCH$_3$), 3.40 [—OCH$_2$CH$_2$CH$_2$CH$_3$]

Mass (FAB); m/z=1009 (MH+)

(3) Following a procedure similar to that of Example 1(3), there was obtained 1.00 g of 2',4"-O-bis-(trimethylsilyl)-(trimethylsilyl)-6-O-methylerythromycin A 9-[O-(1-n-butoxy-1-methylethyl)oxime] from 1 g of the compound obtained above.

$^1$H-NMR (CDCl$_3$); δ (ppm)=0.08 (2'—O—TMS), 0.14 (4"—O—TMS), 2.21 [3'—N(CH$_3$)$_2$], 3.06 (6—OCH$_3$), 3.30 (3"—OCH$_3$)

$^{13}$C-NMR (CDCl$_3$); δ (ppm)=0.9 (4"—O—TMS), 1.1 (2'—O—TMS), 41.0 [3'—N(CH$_3$)$_2$], 49.7 (3"—OCH$_3$), 102.7 [—O—C(CH$_3$)$_2$O—]

Mass (FAB); m/z=1023 (MH+)

EXAMPLE 14

(1) To a solution of 10 g of erythromycin A 9-oxime in 70 ml of dichloromethane were added under ice-cooling 2.3 g of pyridine hydrochloride and then a solution of 8.58 g of 1-methoxy-1-cyclohexene in 30 ml of dichloromethane. After stirring at room temperature overnight, the reaction solution was poured into 100 ml of 2N aqueous sodium hydroxide solution and extracted with dichloromethane. The organic layer was washed with, in turn, water and a saturated aqueous sodium chloride solution and dried over anhydrous magnesium sulfate. The solvent was evaporated under reduced pressure, and the residue was purified by silica gel column chromatography (eluent, chloroform:methanol:aqueous ammonia=10:1:0.1) and recrystallized from chloroform - diisopropyl ether to give 2.40 g of erythromycin A 9-[O-(1-methoxycyclohexyl)oxime].

m.p. 117°-118° C.

$^1$H-NMR (CDCl$_3$); δ (ppm)=2.28 [3'—N(CH$_3$)$_2$], 3.20

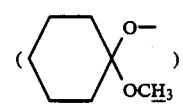

3.32 (3"—OCH$_3$)

$^{13}$C-NMR (CDCl$_3$); δ (ppm)=40.30 [3'—N(CH$_3$)$_2$], 48.39

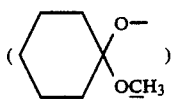

49.50 (3″—OCH₃)

Mass (FAB); m/z=861 (MH+)

(2) To a solution of 2.2 g of the compound, obtained above, in 11 ml of N,N-dimethylformamide were added under ice-cooling 1.65 g of 1,1,1,3,3,3-hexamethyldisilazane and then 0.44 g of pyridine hydrochloride, and the mixture was stirred at room temperature for 4 hours. Then, following a procedure similar to that of Example 10(1), there was obtained 2.55 g of 2′, 4″-O-bis(trimethylsilyl)-erythromycin A 9-[O-(1-methoxycyclohexyl)oxime].

¹H—NMR (CDCl₃); δ (ppm)=0.10 (2′—O—TMS), 0.15 (4″-O—TMS) 2.24 [3′—N(CH₃)₂], 3.20

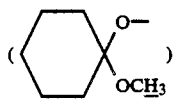

3.30 (3″OCH₃)

¹³C-NMR (CDCl₃); δ (ppm)=0.91 (4″—O—TMS), 1.02 (2′—O—TMS) 41.00 [3′—N(CH₃)₂], 48.33

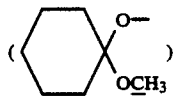

49.74 (3″-OCH₃)

Mass (CI); m/z=1005 (MH+)

(3) To a solution of 2.2 g of the compound, obtained above, in 22 ml of a mixture of dimethyl sulfoxide and tetrahydrofuran (1:1), were added under ice-cooling 0.23 ml of methyl iodide and 190 mg of 85% potassium hydroxide powder, and the mixture was stirred at room temperature for 3 hours. Then, following a procedure similar to that of Example 1(3), there was obtained 2.01 g of 2′,4″-O-bis (trimethylsilyl)-6-O-methylerythromycin A 9-[O-(1methoxycyclohexyl)oxime].

¹H-NMR (CDCl₃); δ (ppm)=0.10 (2′-O-TMS), 0.14 (4″-O-TMS) 2.21 [3′-N(CH₃)₂], 3.11 (6-OCH₃) 3.21

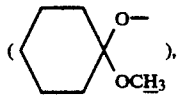

3.31 (3″—OCH₃)

¹³C-NMR (CDCl₃); δ (ppm)=0.90 (4″—O—TMS), 1.06 (2′-O-TMS) 40.98 [3′-N(CH₃)₂], 48.10

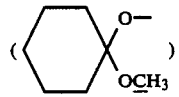

49.71 (3″—OCH₃), 51.17 (6—OCH₃)

Mass (CI); m/z=1019 (MH+)

EXAMPLE 15

To a solution of 1 g of erythromycin A 9-oxime in 10 ml of dichloromethane were added 0.23 g of pyridine hydrochloride and then a solution of 1.1 g of 1,1-dimethoxycyclohexane in 3 ml of dichloromethane, and the mixture was stirred at room temperature for 24 hours. Then, following a procedure similar to that of Example 9, there was obtained 0.65 g of erythromycin A 9-[O-(1-methoxycyclohexyl)oxime], which was identical to the compound obtained in Example 14(1).

EXAMPLE 16

(1) To a solution of 5 g of erythromycin A 9-oxime and 1.16 g of pyridine hydrochloride in 25 ml of dichloromethane was added dropwise under ice-cooling 11.1 ml of triethyl orthoformate. After the reaction, stirring was continued at room temperature for 4.5 hours, Then, following a procedure similar to that of Example 14(1), the resulting crude product was purified by silica gel column chromatography (eluent, acetone:n-hexane:triethylamine=3:10:0.2) to give 3.44 g of erythromycin A 9-[O-(diethoxymethyl)oxime].

¹H-NMR (CDCl₃); δ (ppm)=2.28 [3′-N(CH₃)₂], 3.32 (3″—OCH₃), 5.64 [—CH(OC₂H₅)₂]

¹³C-NMR (CDCl₃); δ (ppm)=40.3 [3′—N(CH₃)₂], 49.5 (3″—OCH₃), 60.9 and 62.5 [—OCH(OCH₂CH₃)₂] 115.7 [—OCH(OC₂H₅)₂]

Mass (FAB); m/z=851 (MH+)

(2) Following a procedure similar to that of Example 5(2) using a solution of 2.5 g of the compound, obtained above, in 25 ml of dichloromethane, 0.86 ml of trimethylsilylimidazole and 0.75 ml of trimethylchlorosilane, the resulting product was purified by silica gel column chromatography (eluent, acetone:n-hexane:triethylamine=1:5:0.01) to give 1.55 g of 2′,4″-O-bis(trimethylsylyl)-erythromycin A 9-[O-(diethoxymethyl)oxime].

m.p. 98°-103° C. (recrystallized from n-hexane)

¹H-NMR (CDCl₃); δ (ppm)=0.1 (2′—O—TMS), 0.15 (4″-O-TMS), 2.23 [3′—N(CH₃)₂], 3.30 (3″—OCH₃), 5.65 [—CH(OC₂H₅)₂]

¹³C-NMR (CDCl₃); δ (ppm)=0.9 (4″—O—TMS), 1.0 (2′-O—TMS), 41.0 [3′—N(CH₃)₂], 49.8 (3″—OCH₃), 60.8 and 62.3 [—OCH(OCH₂CH₃)₂], 115.7 [—OCH(OC₂H₅)₂]

Mass (FAB); m/z=995 (MH+)

(3) Following a procedure similar to that of Example 5(3) using 1 g of the compound obtained above, there was obtained 0.99 g of 2′,4″-O-bis(trimethylsilyl)-6-O-methylerythromycin A 9-[O-(diethoxymethyl)oxime].

¹H-NMR (CDCl₃); δ (ppm)=0.09 (2′—O—TMS), 0.15 (4″—O—TMS), 2.21 [3′—N(CH₃)₂], 3.10 (6-OCH₃), 3.30 (3″—OCH₃), 5.65 [—CH(OC₂H₅)₂]

¹³C-NMR (CDCl₃); δ (ppm)=0.9 (4″—O—TMS), 1.1 (2′—O—TMS), 41.0 [3′—N(CH₃)₂], 49.7 (3″—OCH₃), 50.9 (6—OCH₃), 60.2 and 61.4 [—OCH(OCH₂CH₃)₂], 115.9 [—OCH(OC₂H₅)₂]

Mass (FAB); m/z=1009 (MH+)

EXAMPLE 17

Following a procedure similar to that of Example 10(2) using 1 g of 2′,4″-O-bis(trimethylsilyl)erythromycin A 9-oxime, obtained in Example 10(1), 1.86 ml of triethyl orthoformate and 194 mg of pyridine hydrochloride, there was obtained 0.60 g of 2′,4‴—O—bis(-trimethylsilyl)erythromycin A 9-[O-(diethoxymethyl- )oxime], which was identical to the compound obtained in Example 16(2).

EXAMPLE 18

To a solution of 10 g of erythromycin A 9-oxime in 50 ml of N,N-dimethylformamide were added 1.07 g of ammonium chloride and then 5.6 ml of 1,1,1,3,3,3-hexamethyldisilazane, and stirring was continued at room temperature for 20 hours. Then, following the procedure similar to that of Example 10(1), there was obtained 11.0 g of 2',4"-O-bis(trimethylsilyl)-erythromycin A 9-oxime, which was identical to the compound obtained in Example 10(1).

EXAMPLE 19

To a solution of 5 g of erythromycin A 9-oxime in 100 ml of dichloromethane were added 5 ml of isopropyl alcohol, 6.4 ml of 2-methoxypropene and 1.15 g of pyridine hydrochloride, and the mixture was stirred at room temperature for 1 hour. To the reaction solution was added saturated aqueous sodium bicarbonate solution, and the mixture was extracted with chloroform. The organic layer was washed with saturated aqueous sodium chloride solution and dried over anhydrous magnesium sulfate. The solvent was evaporated under reduced pressure to give 5.4 g of erythromycin A 9-{O-[1-(1-methylethoxy)-1-methylethyl]oxime}, which was identical to the compound obtained in Example 5(1).

EXAMPLE 20

(1) To a solution of 7.49 g of erythromycin A 9-oxime in 100 ml of dichloromethane were added 10.4 ml of cyclohexyl alcohol, 9.6 ml of 2-methoxypropene and 1.74 g of pyridine hydrochloride, and the mixture was stirred at room temperature for 1 hour. Then, following a procedure similar to that of Example 19, the resulting residue was purified by silica gel column chromatography (eluent, acetone:n-hexane:triethylamine=1:5:0.1–3:10:0.2) and recrystallized from aqueous acetone to give 5.7 g of erythromycin A 9-[O-(1-cyclohexyloxy-1-methylethyl)oxime].

m.p 107°-109.5° C.

$^1$H-NMR (CDCl$_3$); δ (ppm)=2.29 [3'—N(CH$_3$)$_2$], 3.30 (3"—OCH$_3$), $^{13}$C-NMR (CDCl$_3$); δ (ppm)=40.1 [3'—N(CH$_3$)$_2$], 49.3 (3"—OCH$_3$), 70.8 [—O—CH(CH$_2$)$_5$], 103.7 [—O—C(CH$_3$)$_2$O—]

Mass (FAB); m/z=889 (MH+)

(2) To a solution of 3 g of the compound, obtained above, in 30 ml of ethyl acetate was added a solution of 1.2 ml of trimethylsilylimidazole and 0.72 ml of trimethylchlorosilane in 5 ml of ethyl acetate, and the mixture was stirred at room temperature for 10 minutes. Then, following a procedure similar to that of Example 5(2), there was obtained 3.22 g of 2',4"-O-bis(trimethylsilyl)erythromycin A 9-[O-(1-cyclohexyloxy-1-methylethyl)oxime].

m.p. 98°-103° C. (recrystallized from n-hexane)

$^1$H-NMR (CDCl$_3$); δ (ppm)=0.10 (2'—O—TMS), 0.15 (4"—O—TMS), 2.24 [3'—N(CH$_3$)$_2$], 3.32 (3"—OCH$_3$), $^{13}$C-NMR (CDCl$_3$); δ (ppm)=0.9 (4"—O—TMS), 1.0 (2'—O—TMS), 40.9 [3'—N(CH$_3$)$_2$], 49.7 (3"—OCH$_3$), 70.7 (—O—CH(CH$_2$)$_5$), 103.8 [—O—C(CH$_3$)$_2$O—]

Mass (CI); m/z=1033 (MH+)

(3) Following a procedure similar to that of Example 1(3) using a solution of 2 g of the compound, obtained above, in 100 ml of a mixture of dimethyl sulfoxide and tetrahydrofuran (1:1), 0.18 ml of methyl iodide and 160 mg of 85% potassium hydroxide powder, the resulting residue was recrystallized from acetone to give 1.2 g of 2',4"-O-bis(trimethylsilyl)-6-O-methylerythromycin A 9-[O-(1-cyclohexyloxy-1-methylethyl)oxime].

m.p. 202°-203° C. (recrystallized from acetone)

$^1$H-NMR (CDCl$_3$); δ (ppm)=0.08 (2'—O—TMS), 0.14 (4"—O—TMS), 2.22 [3'—N(CH$_3$)$_2$], 3.07 (6—OCH$_3$), 3.32 (3"—OCH$_3$)

$^{13}$C—NMR (CDCl$_3$); δ (ppm)=0.8 (4"—O—TMS), 0.9 (2'—O—TMS), 40.9 [3'-N(CH$_3$)$_2$], 49.6 (3"—OCH$_3$), 50.8 (6—OCH$_3$), 70.0 (—O—CH(CH$_2$)$_5$], 103.0 [—O'13 C(CH$_3$)$_2$O—]

Mass (EI); m/z=1046 (M+)

EXAMPLE 21

(1) To a solution of 7 g of 2',4"-O-bis(trimethylsilyl)-erythromycin A 9-oxime, obtained in Example 10(1), in 35 ml of dichloromethane were added under ice-cooling 1.36 g of pyridine hydrochloride and then a solution of 3.41 g of 2,2-diisopropoxybutane in 14 ml of dichloromethane, and the mixture was stirred at room temperature for 1.5 hours. Then, following a procedure similar to that of Example 10(2), there was obtained 7.5 g of 2',4"-O-bis(trimethylsilyl)-erythromycin A 9-{O-[1-(1-methylethoxy)-1-methylpropyl]oxime}.

$^1$H-NMR (CDCl$_3$); δ (ppm)=0.10 (2'—O—TMS), 0.15 (4"—O—TMS), 2.24 [3'—N(CH$_3$)$_2$], 3.31 (3"—OCH$_3$), 4.03 [—O—CH(CH$_3$)$_2$]

$^{13}$C-NMR (CDCl$_3$); δ (ppm)=0.92 (4"—O—TMS), 1.02 (2'—O—TMS), 8.60

41.00 [3'N(CH$_3$)$_2$], 49.73 (3"—OCH$_3$), 106.05 [—O—CCH (C$_2$H$_5$)—]

Mass (CI); m/z=1007 (MH+)

(2) Following a procedure similar to that of Example 1(3) using a solution of 4 g of the compound, obtained above, in 40 ml of a mixture of dimethyl sulfoxide and tetrahydrofuran (1:1), 0.73 g of methyl iodide and 245 mg of 85% potassium hydroxide powder, there was obtained 3.87 g of 2',4"-O-bis(trimethylsilyl)-6-O-methylerythromycin A 9-{O-[1-(1-methylethoxy)-1-methylpropyl]oxime}.

$^1$H-NMR (CDCl$_3$); δ (ppm)=0.10 (2'—O—TMS), 0.15 (4"—O—TMS), 2.23 [3'—N(CH$_3$)$_2$], 3.09 (6—OCH$_3$), 3.33 (3"—OCH$_3$)

C-NMR (CDCl$_3$); δ (ppm)=0.91 (4"—O—TMS), 1.07(2'—O—TMS), 8.64 and 8.83

41.00 [3'—N(CH$_3$)$_2$], 49.71 (3"—OCH$_3$), 50.95 and 51.19 (6—OCH$_3$), 105.62 [—O—CCH$_3$(C$_2$H$_5$)—]

Mass (CI); m/z=1021 (MH+)

EXAMPLE 22

To a solution of 1 g of erythromycin A 9-oxime in 7 ml of dichloromethane were added under ice-cooling 0.23 g of pyridine hydrochloride and a solution of 2.51 g of 2,2-di-n-butoxypropane in 3 ml of dichloromethane, and the mixture was stirred at room temperature for 24 hours. Then, following a procedure similar to that of Example 10(2), there was obtained 0.83 g of erythromycin A 9-[O-(1-n-butoxy-1-methylethyl)oxime], which was identical to the compound obtained in Example 13(1).

EXAMPLE 23

To a solution of 1 g of 2',4''-O-bis(trimethylsilyl)erythromycin A 9-oxime, obtained in Example 10(1), in 7 ml of dichloromethane were added under ice-cooling 194 mg of pyridine hydrochloride and then 2.11 g of 2,2-di-n-butoxypropane, and the mixture was stirred at room temperature for 5 hours. Then, following a procedure similar to that of Example 10(2), there was erythromycin A 9-[O-(1-n-butoxy-1-methylethyl)oxime], which was identical to the compound obtained in Example 13(2).

EXAMPLE 24

(1) To a solution of 2.48 g of erythromycin A 9-oxime in 17 ml of dichloromethane were added 0.58 g of pyridine hydrochloride and then a solution of 1.7 g of 2-methylenetetrahydrofuran in 7.5 ml of dichloromethane, and the mixture was stirred at room temperature for 3 hours. Then, following a procedure similar to that of Example 5(1), the resulting product was purified by silica gel column chromatography (eluent, acetone:n-hexane:triethylamine=3:10:0.2) to give 2.25 g of erythromycin A 9-[O-(2-methyl-2-tetrahydrofuryl)oxime].

$^1$H-NMR (CDCl$_3$); δ (ppm)=1.54 and 1.55 [—OC(CH$_3$)$_2$O—], 2.29 [3'—N(CH$_3$)$_2$], 3.32 (3''—OCH$_3$)

$^{13}$C-NMR (CDCl$_3$); δ (ppm)=23.82 and 24.62 [OC(CH$_3$)O—], 40.32 [3'—N(CH$_3$)$_2$], 49.49 (3''—OCH$_3$), 68.90 (—OCH$_2$—)

(2) To a solution of 2 g of the compound, obtained above, in 10 ml of N,N-dimethylformamide were added under ice-cooling 416 mg of pyridine hydrochloride and 970 mg of 1,1,1,3,3,3-hexamethyldisilazane, and the mixture was stirred at room temperature for 6 hours. Then, following a procedure similar to that of Example 10(1), there was obtained 2.18 g of 2',4''-O-bis(trimethylsilyl)erythromycin A 9-[O-(2-methyl-2-tetrahydrofuryl)oxime].

$^1$H-NMR (CDCl$_3$); δ (ppm)=0.10 (2'—O—TMS), 0.15 (4''—O—TMS), 1.54 and 1.55 [—OC(CH$_3$)$_2$O—], 2.23 [3'—N(CH$_3$)$_2$], 3.30 (3''—OCH$_3$)

$^{13}$C-NMR (CDCl$_3$); δ (ppm)=1.46 (4''—O—TMS), 1.56 (2'—O—TMS), 24.31 and 24.94 [OC(CH$_3$)O—], 41.54 [3'—N(CH$_3$)$_2$], 50.28 (3''—OCH$_3$), 69.37 (—OCH$_2$—)

Mass (CI); m/z=977 (MH+)

Following a procedure similar to that of Example 1(3) using a solution of 1.9 g of the compound, obtained above, in 19 ml of a mixture of dimethyl sulfoxide and tetrahydrofuran (1:1), 360 mg of methyl iodide and 154 mg of 85% potassium hydroxide powder, there was obtained 1.64 g of 2',4''-O-bis(trimethylsilyl)-6-O-methylerythromycin A 9-[O-(2-methyl-2-tetrahydrofuryl)-oxime].

$^1$H-NMR (CDCl$_3$); δ (ppm)=0.09 (2'—O—TMS), 0.15 (4''—O—TMS), 1.53 and 1.56 [O—C(CH$_3$)O—], 2.21 [3'—N(CH$_3$)$_2$], 3.08 (6—OCH$_3$), 3.31 (3''—OCH$_3$)

$^{13}$C-NMR (CDCl$_3$); δ (ppm)=0.90 (4''—O—TMS), 1.06 (2'—O—TMS), 23.53 and 24.17 [OC(CH$_3$)O—], 40.99 [3'—N(CH$_3$)$_2$], 49.72 (3''—OCH$_3$), 50.91 (6—OCH$_3$), 69.08 (—OCH$_2$—)

Mass (CI); m/z=991 (MH+)

EXAMPLE 25

To a solution of 4.45 g of erythromycin A 9-oxime in 31 ml of dichloromethane were added 1.03 g of pyridine hydrochloride and then a solution of 4.75 g of 5-methyl-2,3-dihydrofuran in 13 ml of dichloromethane, and the mixture was stirred at room temperature for 24 hours. Then, following a procedure similar to that of Example 5(1), there was obtained 3.0 g of erythromycin A 9-[O-(2-methyl-2-tetrahydrofuryl)oxime], which was identical to the compound obtained in Example 24(1).

EXAMPLE 26

To a solution of 3.86 g of 2',4''—O—bis)trimethylsilyl)-erythromycin A 9-[O-(1-methoxy-1-methylethyl)oxime], obtained in Example 1(2), in 200 ml of a mixture of dimethyl sulfoxide and tetrahydrofuran (1:1) were added 1.6 ml of ethyl iodide and 780 mg of 85% potassium hydroxide powder, and the mixture was stirred at room temperature for 1.5 hours. Then, following a procedure similar to that of Example 1(3), the resulting residue was recrystallized from methanol to give 1.55 g of 2',4''-O-bis(trimethylsilyl)-6-O-ethylerythromycin A 9-[O-(1-methoxy-1-methylethyl)oxime].

Mass (FAB);

m/z=993 (MH+)

EXAMPLE 27

(1) To a solution of 3.74 g of erythromycin A 9-oxime in 150 ml of dichloromethane were added 3.0 ml of ethyl vinyl ether and 1.73 g of pyridine hydrochloride, and the mixture was stirred at room temperature for 1 week. Then, following a procedure similar to that of Example 1(1), there was obtained 3.5 g of erythromycin A 9-[O-(1-ethoxyethyl)oxime].

$^1$H-NMR (CDCl$_3$); δ (ppm)=1.42 [—OCH(CH$_3$)O—], 2.30 [3'-N(CH$_3$)$_2$], 3.34 (3''—OCH$_3$)

$^{13}$C-NMR (CDCl$_3$); δ (ppm)=15.5 (—OCH$_2$CH$_3$), 20.2 [—OCH(CH$_3$)O—]40.3 [3'—N(CH$_3$)$_2$], 49.5 (3''—OCH$_3$), Mass (FAB); m/z=821 (MH+)

(2) To a solution of 820 mg of the compound, obtained above, in 5 ml of N,N-dimethylformamide were added 0.41 ml of 1,1,1,3,3,3-hexamethyldisilazane and 80 mg of ammonium chloride, and the mixture was stirred at room temperature for 4 hours. Then, following a procedure similar to that of Example 10(1), there was obtained 700 mg of 2',4''-O-bis(trimethylsilyl)-erythromycin A 9-[O-(1-ethoxyethyl)oxime].

$^1$H-NMR (CDCl$_3$); δ (ppm)=0.10 (2'—O—TMS), 0.15 (4''—O—TMS), 1.53 [0—CH(CH$_3$)O—], 2.20 [3'—N(CH$_3$)$_2$], 3.31 (3''—OCH$_3$)

Mass (FAB); m/z=965 (MH+)

(3) To a solution of 650 mg of the compound, obtained above, in 14 ml of a mixture of dimethyl sulfoxide and tetrahydrofuran (1:1) were added under ice-cooling 0.06 ml of methyl iodide and 58 mg of 85% potassium hydroxide powder, and the mixture was stirred at room temperature for 2 hours. Then, following a procedure similar to that of Example 1(3), there was obtained 610 mg of 2',4''-O-bis(trimethylsilyl)-6-O-methylerythromycin A 9-[O-(1-ethoxyethyl)oxime].

$^1$H-NMR (CDCl$_3$); δ (ppm)=0.09 (2'—O—TMS), 0.16 (4''—O—TMS), 1.10 [O—CH(CH$_3$)O—], 2.22 [3'—N(CH$_3$)$_2$], 3.07 (6—OCH$_3$), 3.32 (3''—OCH$_3$)

Mass (FAB); m/z=979 (MH+)

EXAMPLE 28

(1) To a solution of 804 mg of 2',4"-O-bis(trimethylsilyl)-erythromycin A 9-oxime, obtained in Example (1), and 156 mg of pyridine hydrochloride in 4 ml of dichloromethane was added under ice-cooling a solution of 338 mg of 3,3-diisopropoxypentane in 1.6 ml of dichloromethane, and the mixture was stirred at room temperature for 6 hours. Then, following a procedure similar to that of Example 10(2), there was obtained 860 mg of 2',4"-O-bis(trimethylsilyl)-erythromycin A 9-{O-[1-(1-methylethoxy)-1-ethylpropyl]oxime}.

$^1$H-NMR (CDCl$_3$) δ (ppm)=0.11 (2'—O—TMS), 0.15 (4"—O—TMS), 2.25 [3'—N(CH$_3$)$_2$], 3.30 (3"—OCH$_3$), 4.04 [—O—CH(CH$_3$)$_2$]

$^{13}$C-NMR (CDCl$_3$); δ (ppm)=0.91 (4"—O—TMS), 1.02 (2'—O—TMS), 40.99 [3'—N(CH$_3$)$_2$], 49.73 (3"—OCH$_3$), 108.32 [—O—C(C$_2$H$_5$)$_2$O—]

Mass (FAB); m/z=1021 (MH+)

(2) To a solution of 669 mg of the compound, obtained above, in 6.6 ml of a mixture of dimethyl sulfoxide and tetrahydrofuran (1:1) were added under ice-cooling 0.06 ml of methyl iodide and 55 mg of 85% potassium hydroxide powder, and the mixture was stirred at room temperature for 2 hours. Then, following a procedure similar to that of Example 1(3), there was obtained 630 mg of 2',4"-O-bis(trimethylsilyl)-6-O-methyl erythromycin A 9-{O-[1-(1-methylethoxy)-1-ethylpropyl]-oxime}.

$^1$H-NMR (CDCl$_3$); δ (ppm)=0.11 (2'—O—TMS), 0.15 (4"—O—TMS), 2.27 [3'—N(CH$_3$)$_2$], 3.10 (6—OCH$_3$), 3.31 (3"—OCH$_3$), 4.10 [—O—CH(CH$_3$)$_2$]

$^{13}$C-NMR (CDCl$_3$); δ (ppm)=0.91 (4"—O—TMS), 1.13 (2'—O—TMS), 40.99 [3'—N(CH$_3$)$_2$], 49.70 (3"—OCH$_3$), 51.22 (6—OCH$_3$), 107.87 [—O—C(C$_2$H$_5$)$_2$O—]

Mass (FAB); m/z=1035 (MH+)

EXAMPLE 29

(1) To a solution of 468 mg of erythromycin A 9-oxime in 5 ml of dichloromethane were added 108 mg of pyridine hydrochloride and then a solution of 367 mg of 2-benzyloxypropene in 2 ml of dichloromethane, and the mixture was stirred at room temperature for 2.5 hours. Then, following a procedure similar to that of Example 1(1), the resulting residue was purified by silica gel column chromatography (eluent, chloroform:methanol:aqueous ammonia=30:1:0.1–10:1:0.1) to give 510 mg of erythromycin A 9-[O-(1-benzyloxy-1-methylethyl)-oxime].

$^1$H-NMR (CDCl$_3$); δ (ppm)=2.28 [3'—N(CH$_3$)$_2$], 3.32 (3"O—CH$_3$), 4.50 (—OCH$_2$C$_6$H$_5$), 7.20-7.40 (—O—CH$_2$C$_6$H$_5$)

8 Mass (FAB): m/z=897 (MH+)

(2) To a solution of 470 mg of the compound obtained above and 90 mg of pyridine hydrochloride in 4 ml of N,N-dimethylformamide was added a solution of 294 mg of 1,1,1,3,3,3-hexamethyldisilazane in 1 ml of N,N-dimethylformamide, and the mixture was stirred at room temperature overnight. Then, following a procedure similar to that of Example 10(1), there was obtained 503 mg of 2', 4"—O—bis(trimethylsilyl)-erythromycin A 9-[O-(1-benzyloxy-1-methylethyl)oxime].

$^1$H-NMR (CDCl$_3$); δ (ppm)=0.10 (2'—OTMS), 0.15 (4"—OTMS), 2.22 [3'—N(CH$_3$)$_2$], 3.30 (3"—OCH3), 4.50 (—OCH$_2$C$_6$H$_5$), 7.20-7.40 [—OCH$_2$C$_6$H$_5$]

Mass (FAB); m/z=1041 (MH+)

(3) To a solution of 388 mg of the compound obtained above and 0.035 ml of methyl iodide in 5 ml of a mixture of dimethyl sulfoxide and tetrahydrofuran (1:1) was added under ice-cooling 29 mg of 85% potassium hydroxide powder, and the mixture was stirred at room temperature for 2 hours. Then, following a procedure similar to that of Example 1(3), there was obtained 376 mg of 2', 4"—O—bis(trimethylsilyl)-6-O-methylerythromycin A 9-[O-(1-benzyloxy-1-methylethyl)oxime].

$^1$H-NMR (CDCl$_3$); δ (ppm)=0.10 (2'—OTMS), 0.15 (4"—OTMS), 2.22 [3'—N(CH$_3$)$_2$], 3.10 (6—O—CH$_3$), 3.32 (3"—O—CH$_3$), 4.52 (—O—CH$_2$C$_6$H$_5$), 7.20-7.40 (—O—CH$_2$C$_6$H$_5$)

Mass (FAB); m/z=1055 (MH+)

Referential Example 1

(1) To a solution of 3.46 g of 2', 4"—O—bis(trimethylsilyl)-6-O-methylerythromycin A 9-[O-(1-methoxy-1-methylethyl)oxime], obtained in Example 1(3), in 60 ml of ethanol/water (1/1) was added 1.5 ml of 99% formic acid, and the mixture was stirred at room temperature for 30 minutes. Then, most of the ethanol was evaporated under reduced pressure, and water was added to the residue. The mixture was made basic with 2N aqueous sodium hydroxide solution and extracted with ethyl acetate. The organic layer was washed with, in turn, water and a saturated aqueous sodium chloride solution and dried over anhydrous magnesium sulfate. The solvent was evaporated under reduced pressure to give 2.53 g of 6-O-methylerythromycin A 9-oxime.

m.p. 248°–251° C. (recrystallized from ethanol - petroleum ether)

(2) To a solution of 2 g of the compound, obtained above, and 1.1 g of sodium hydrogen sulfite in 20 ml of ethanol/water (1/1) was added 0.25 ml of 99% formic acid, and the mixture was refluxed for 100 minutes. To the reaction solution was added 30 ml of water, 5 ml of 2N aqueous sodium hydroxide solution was added dropwise, and then the mixture was stirred under ice-cooling for 2 hours. The precipitate which formed was collected by filtration and recrystallized from ethanol to give 1.51 g of 6—O—methylerythromycin A.

m.p. 223°-225° C.

Referential Example 2

To a solution of 9.8 g of 2', 4"—O—bis(trimethylsilyl)-6—O—methylerythromycin A 9-[O-(1-methoxy-1methylethyl)oxime]obtained in Example 1(3), in 100 ml of ethanol/water (1/1) were added 6.7 g of sodium hydrogen sulfite and 1.6 ml of 99% formic acid, and then the mixture was refluxed with stirring for 60 minutes. To the reaction solution was added 150 ml of water, and then the mixture was adjusted to pH about 10 by adding dropwise 2N aqueous sodium hydroxide solution and stirred under ice-cooling for 1 hour. The precipitate which formed was collected by filtration, washed with water and recrystallized from ethanol to give 5.15 g of 6—O—methylerythromycin A, which was identical to the compound obtained in Referential Example 1(2).

Referential Example 3

To a solution of 980 mg of 2', 4"—O—bis(triethylsilyl)-6—O-ethylerythromycin A 9-[O-(1-methoxy-1-methylethyl)oxime], obtained in Example 26, in 10 ml of ethanol/water (1/1) were added 2 g of sodium hydrogen sulfite and 0.23 ml of 99% formic acid, and the mixture was refluxed with stirring for 60 minutes. Then, following a procedure similar to that of Referential Example 2, the resulting residue was recrystallized from ethanol to give 610 mg of 6-O-ethylerythromycin A.

m.p. 213.5°-214.5° C;

¹H-NMR (CDCl₃); δ (ppm)=1.01 (6—OCH₂CH₃), 2.23 [3'—N(CH₃)₂], 3.33 (3''—OCH₃), 3.45 (6—OCH₂CH₃)

Mass (FAB); m/z=761 (MH⁺)

EXAMPLE 30

(1) To a solution of 5 g of erythromycin A O-oxime in 35 ml of dichloromethane were added under ice-cooling 1.16 g of pyridine hydrochloride and then a solution of 6.69 g of 1,1-diisopropoxycyclohexane in 15 ml of dichloromethane, and the mixture was stirred at room temperature for 42.5 hours. Then, following the procedure similar to that of Example 9, there was obtained 5.1 g of erythromycin A 9-{O-[1-(1-methylethoxy)cyclohexyl]oxime} m.p. 114°-116° C. (recrystallized from dichloromethane - isopropyl ether)

¹H-NMR (CDCl₃); δ (ppm)=2.32 [3'—N(CH₃)₂], 3.32 (3''—OCH₃),2]4.05 [—OCH(CH₃)₂]

¹³C-NMR (CDCl₃) ; δ (ppm)=24.33 [—OCH(CH₃)₂], 40.31 [3'—N(CH₃)₂], 49.49 (3''—OCH₃), 63.68 [—OCH(CH₃)₂],

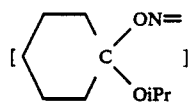

MASS (SIMS); m/z=889 (MH⁺)

To a solution of 4.45 g of the compound, obtained above, in 15 ml of N,N-dimethylformamide were added 0.58 g of pyridine hydrochloride and then under ice-cooling 1.76 ml of 1,1,1,3,3,3,-hexamethyldisilazane, and the mixture was stirred at room temperature for 5 hours and 40 minutes. Then, following a procedure similar to that of Example 10(1), there was obtained 3.78 g of 2',4''—O—bis(trimethylsilyl)erythromycin A 9-{O-[1-(1-methlethoxy)cyclohexyl]oxime}.

¹H-NMR (CDCl₃); δ (ppm)=0.08 (2'—O—TMS), 0.12 (4''—O—TMS), 2.20 [3'—N(CH₃)₂], 3.28 (3''—OCH₃), 4.05 [—OCH(CH₃)₂)

¹³C-NMR(CDCl₃); δ (ppm)=0.91 (4''—O—TMS),1.00 (2'—O—TMS), 24.35 [—OCH(CH₃)₂, 40.99 [3'—N(CH₃) ₂], 63.24 [—OCH(CH₃)₂],

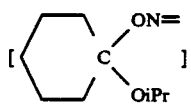

MASS (CI); m/z=1032 (M⁺)

EXAMPLE 31

(1) To a solution of 9.8 g of 2',4''O—bis(trimethylsilyl)erythromycin A 9-oxime, obtained by the procedure of Example 10(1), in 45 ml of dichloromethane were added under ice-cooling 1.73 g of pyridine hydrochloride and then a solution of 5.0 g of 1,1-diisopropoxycyclohexane in 15 ml of dichloromethane, and the mixture was stirred at room temperature for 18 hours and 40 minutes. Then, following the procedure of that of Example 9, there was obtained 10.7 g of 2',4''O—bis(trimethylsilyl)erythromycin A 9-{O-[1-(1-methylethoxy)cyclohexyl]oxime}which was identical with the compound obtained in Example 30(2).

(2) To a solution of 5.86 g of the compound, obtained above, in 53 ml of a mixture of dimethyl sulfoxide and tetrahydrofuran (1:1) were added under ice-cooling 0.915 g of methyl iodide and then 0.38 g of 95% potassium hydorxide powder, and the mixture was stirred at room temperature for 5 hours. Then, following a procedure similar to that of Example 1(3), there was obtained 5.64 g of 2', 40''—O—bis(trimethylsilyl)-6—O—methylerythromycin A 9-{O-[1-(1methylethoxy)cyclohexyl]oxime}.

¹H-NMR (CDCl₃); δ (ppm)=0.09 (2'—O—TMS), 0.15 (4''—O—TMS), 2.21 [3''—N(CH₃)₂], 3.10 (6—OCH(CH₃)₂, 3.30 (3''OCH₃), 4.10 [—OCH(CH₃)₂), ¹³C-NMR (CDCl₃); δ (ppm)=0.90 (4''—O—TMS), 1.06 (2'—O—TMS), 24.44 and 24.57, [—OCH(CH₃)₂], 41.00 [3'—N(CH₃)₂], 51.11 (6—OCH₃), 62.82 [—OCH(CH₃)₂], 103.62

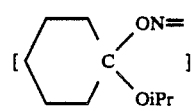

Mass (CI); m/z=1046 (M⁺)

EXAMPLE 32

To a solution of 5 g of erythromycin A 9-oxime in 20 ml of acetonitrile were added 1.16 g of pyridine hydrochloride and then a solution of 3.35 g of 1,1-diisopropoxycyclohexane in 5 ml of acetonitrile, and the mixture was stirred at room temperature for 14.5 hours. To the reaction solution were added under ice-cooling 1.16 g of pyridine hydrochloride and 5.6 ml of 1,1,1,3,3,3hexamethyldisilazane, and the mixture was stirred under ice-cooling for 30 minutes and further stirred at room temperature for 1.5 hours. To the reaction solution were added 60 ml of n-hexane, 5 ml of 2N aqueous sodium hydroxide solution and 50 ml of water, and the organic layer was collected, washed thoroughly with water and dried over anhydrous magnesium sulfate. The solvent was evaporated under reduced pressure to give 6.5 g of 2', 4''—O—bis(trimethylsilyl)-erythromycin A 9-{O-[1-(1-methylethoxy)-cyclohexyl]oxime}, which was identical with the compound obtained in Example 30(2).

EXAMPLE 33

To a solution of 23.4 g of erythromycin A 9-oxime in 160 ml of dichloromethane were added under ice-cooling 5.4 g of pyridine hydrochloride and then a solution of 15.3 g of 1-isopropoxy-1-cyclohexene in 40 ml of dichloromethane, and the mixture was stirred at room temperature overnight. Then, following a procedure similar to that of Example 9, there was obtained 20.5 g of erythromycin A 9-{O-[1-(1-methylethoxy)-cyclohexyl]oxime}, which was identical with the compound obtained in Example 30(1).

What is claimed is:

1. An Erythromycin A derivative represented by the formula:

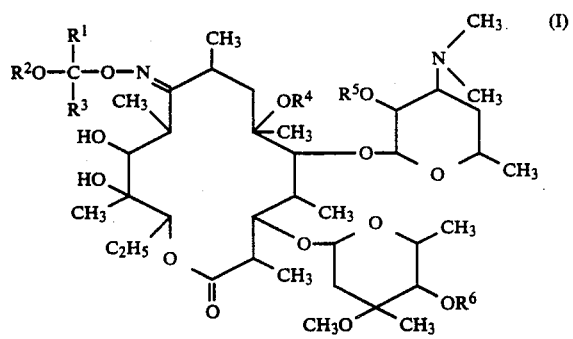

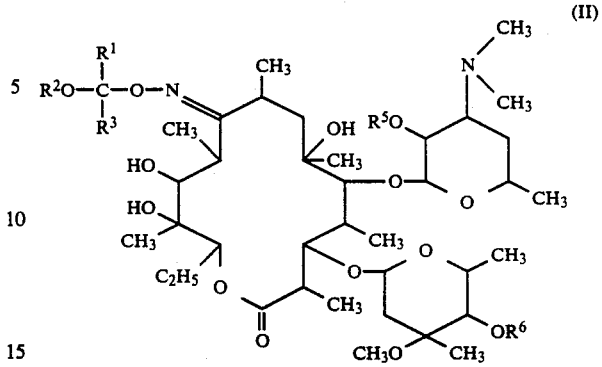

wherein R' is a group of the formula $R^7CH_2$— (wherein $R^7$ is a hydrogen atom or an alkyl group having 1 to 3 carbon atoms) or a group of the formula $R^8O$ (wherein $R^8$ is an alkyl group having 1 to 6 carbon atoms), $R^2$ is $R^8$, a cycloalkyl group having 5 to 7 carbon atoms, a phenyl group or an aralkyl group, or $R^2$ and $R^7$ together form an alkylene group having 2 or 3 carbon atoms, $R^3$ is a hydrogen atom, an alkyl group having 1 to 4 carbon atoms, a phenyl group or an aralkyl group, or $R^3$ and $R^7$ together form an alkylene group having 3 to 5 carbon atoms or an alkylene group having 3 to 5 carbon atoms and substituted by 1 to 3 alkyl groups having each 1 to 3 carbon atoms, or $R^2$ and $R^3$ together form an alkylene group having 3 or 4 carbon atoms, $R^4$ is an alkyl group having 1 to 3 carbon atoms, $R^5$ is a substituted silyl group of formula —$SiR^9R^{10}R^{11}$ (wherein $R^9$, $R^{10}$ and $R^{11}$ are the same or different, and each is a hydrogen atom, an alkyl group having 1 to 15 carbon atoms, a phenyl substituted alkyl group in which the alkyl moiety has 1 to 3 carbon atoms, a phenyl group, a cycloalkyl group having 5 to 7 carbon atoms or an alkenyl group having 2 to 5 carbon atoms, with the proviso that at least one of $R^9$, $R^{10}$ and $R^{11}$ is other than hydrogen atom), and $R^6$ is a hydrogen atom or $R^5$.

2. An Erythromycin A derivative represented by the formula:

wherein $R^1$ is a group of the formula $R^7CH_2$— (wherein $R^7$ is a hydrogen atom of an alkyl group having 1 to 3 carbon atoms) or a group of the formula $R^8O$— (wherein $R^8$ is an alkyl group having 1 to 6 carbon atoms), $R^2$ is $R^8$, a cycloalkyl group having 5 to 7 carbon atoms, a phenyl group or an aralkyl group, or $R^2$ and $R^7$ together form an alkylene group having 2 or 3 carbon atoms, $R^3$ is a hydrogen atom, an alkyl group having 1 to 4 carbon atoms, a phenyl group or an aralkyl group, or $R^3$ and $R^7$ together form an alkylene group having 3 to 5 carbon atoms or an alkylene group having 3 to 5 carbon atoms and substituted by 1 to 3 alkyl groups having each 1 to 3 carbon atoms, or $R^2$ and $R^3$ together form an alkylene group having 3 or 4 carbon atoms, $R^5$ is a substituted silyl group of formula —$SiR^9R^{10}R^{11}$ (wherein $R^9$, $R^{10}$ and $R^{11}$ are the same or different, and each is a hydrogen atom, an alkyl group having 1 to 15 carbon atoms, a phenyl substituted alkyl group in which the alkyl moiety has 1 to 3 carbon atoms, a phenyl group, a cycloalkyl group having 5 to 7 carbon atoms or an alkenyl group having 2 to 5 carbon atoms, with the proviso that at least one of $R^9$, $R^{10}$ and $R^{11}$ is other than hydrogen atom), and $R^6$ is a hydrogen atom or $R^5$.

3. 2',4''-O-bis(trimethylsilyl)-erythromycin A 9-{O-[1-(1-methylethoxy)cyclohexyl]oxime}.

* * * * *

UNITED STATES PATENT AND TRADEMARK OFFICE
CERTIFICATE OF CORRECTION

PATENT NO. : 4,990,602
DATED : February 5, 1991
INVENTOR(S) : Morimoto et al.

It is certified that error appears in the above-identified patent and that said Letters Patent is hereby corrected as shown below:

Column 25,
Line 15, "R'" should read -- $R^1$ --

Column 26,
Line 18, "of" should read -- or --

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 4,990,602
DATED : February 5, 1991
INVENTOR(S) : Morimoto et al.

It is certified that error appears in the above-identified patent and that said Letters Patent is hereby corrected as shown below:

Column 25,
Line 15, "R'" should read -- $R^1$ --

Column 26,
Line 18, "of" should read -- or --

Signed and Sealed this

Eighteenth Day of May, 2004

JON W. DUDAS
*Acting Director of the United States Patent and Trademark Office*